United States Patent
Hartley et al.

(10) Patent No.: US 9,232,320 B2
(45) Date of Patent: Jan. 5, 2016

(54) MODULAR AUDITORY PROSTHESIS SYSTEMS AND METHODS

(75) Inventors: Lee F. Hartley, Valencia, CA (US); Tracey L. Kruger, Saugus, CA (US)

(73) Assignee: Advanced Bionics AG, Staefa (CH)

( * ) Notice: Subject to any disclaimer, the term of this patent is extended or adjusted under 35 U.S.C. 154(b) by 158 days.

(21) Appl. No.: 13/983,559

(22) PCT Filed: Jan. 27, 2012

(86) PCT No.: PCT/US2012/022937
§ 371 (c)(1),
(2), (4) Date: Aug. 3, 2013

(87) PCT Pub. No.: WO2012/106205
PCT Pub. Date: Aug. 9, 2012

(65) Prior Publication Data
US 2013/0308803 A1    Nov. 21, 2013

Related U.S. Application Data

(60) Provisional application No. 61/439,668, filed on Feb. 4, 2011.

(51) Int. Cl.
*H04R 25/00* (2006.01)
*A61N 1/36* (2006.01)

(52) U.S. Cl.
CPC ............ *H04R 25/50* (2013.01); *A61N 1/36032* (2013.01); *H04R 25/558* (2013.01); *H04R 25/556* (2013.01); *H04R 25/60* (2013.01)

(58) Field of Classification Search
CPC .... H04R 25/556; H04R 25/558; H04R 25/30; H04R 25/305; H04R 25/554; H04R 25/60; H04R 25/505

USPC .......... 381/312–321, 328, 323, 330; 607/55–57
See application file for complete search history.

(56) References Cited

U.S. PATENT DOCUMENTS

| 4,467,145 A | 8/1984 | Borstel |
| 4,947,432 A | 8/1990 | Topholm |
| 5,524,056 A | 6/1996 | Killion et al. |

(Continued)

FOREIGN PATENT DOCUMENTS

| AU | WO 2005062668 A1 * | 7/2005 | ......... A61N 1/36032 |
| EP | 0537026 | 4/1993 | |

(Continued)

OTHER PUBLICATIONS

Communication pursuant to Article 94(3) EPC received in European Patent Application No. 12702400.8, dated Nov. 6, 2014.

(Continued)

*Primary Examiner* — Sunita Joshi
(74) *Attorney, Agent, or Firm* — ALG Intellectual Property, LLC (57) ABSTRACT

An exemplary auditory prosthesis system includes a sound processor module configured to process an audio signal and operate in accordance with a plurality of control parameters and an accessory header module configured to be selectively coupled to the sound processor module and facilitate external adjustment of one or more control parameters included in the plurality of control parameters while coupled to the sound processor module. Corresponding systems and methods are also described.

23 Claims, 11 Drawing Sheets

(56) References Cited

U.S. PATENT DOCUMENTS

| | | |
|---|---|---|
| 5,824,022 A | 10/1998 | Zilberman et al. |
| 6,620,094 B2 | 9/2003 | Miller |
| 7,599,500 B1 | 10/2009 | Segel et al. |
| 7,602,929 B2 * | 10/2009 | Topholm ............... H04R 25/556 381/322 |
| 8,364,274 B1 * | 1/2013 | Litvak ............................. 607/57 |
| 8,437,860 B1 | 5/2013 | Crawford et al. |
| 2004/0073275 A1 * | 4/2004 | Maltan ............... A61N 1/36032 607/57 |
| 2005/0008175 A1 | 1/2005 | Hagen et al. |
| 2007/0282394 A1 | 12/2007 | Segel et al. |
| 2008/0288022 A1 | 11/2008 | Van der Borght et al. |
| 2011/0103627 A1 * | 5/2011 | Meier et al. ................... 381/314 |
| 2013/0085549 A1 | 4/2013 | Case et al. |

FOREIGN PATENT DOCUMENTS

| | | |
|---|---|---|
| WO | WO 2009/118221 | 10/2009 |
| WO | WO 2012/096848 | 7/2012 |
| WO | WO 2012106206 | 8/2012 |

OTHER PUBLICATIONS

International Search Report and Written Opinion received in International Application No. PCT/US12/022937 dated Apr. 12, 2012.

* cited by examiner

MODULAR AUDITORY PROSTHESIS SYSTEMS AND METHODS

RELATED APPLICATIONS

The present application claims priority to U.S. Provisional Patent Application No. 61/439,668 by Lee F. Hartley et al., filed on Feb. 4, 2011, and entitled "Modular Auditory Prosthesis Systems and Methods," the contents of which are hereby incorporated by reference in their entirety.

BACKGROUND INFORMATION

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant systems) have been developed. Auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

Conventional auditory prosthesis systems include a sound processing unit worn on or behind the ear of a patient. The sound processing unit typically includes a microphone for detecting sounds in the patient's environment and audio processing circuitry for modifying, digitizing, and/or amplifying the detected sounds. As such, sound processing units worn behind or on the ear are often relatively large, cumbersome, and noticeable by others. They often lack desirable features (e.g., extended battery life and optimal sound processing capabilities) because such features would make them even larger and more cumbersome.

SUMMARY

An exemplary auditory prosthesis system includes a sound processor module configured operate in accordance with a plurality of control parameters and a control header module configured to be selectively coupled to the sound processor module. The control header module includes one or more input facilities configured to adjust one or more control parameters included in the plurality of control parameters in response to manual input while the control header module is coupled to the sound processor module.

Another exemplary auditory prosthesis system includes a sound processor module configured to process an audio signal and operate in accordance with a plurality of control parameters and an accessory header module configured to be selectively coupled to the sound processor module and facilitate external adjustment of one or more control parameters included in the plurality of control parameters while coupled to the sound processor module.

An exemplary method includes a sound processing module 1) operating in accordance with a plurality of control parameters, 2) detecting a hot plugging of a control header module into the sound processing module, the control header module comprising one or more input facilities configured to adjust one or more control parameters included in the plurality of control parameters in response to manual input, 3) providing, in response to the detecting of the hot plugging, power to the control header module, 4) receiving, from the control header module while the control header module is hot plugged into the sound processing module, data representative of an instruction to adjust a control parameter included in the plurality of control parameters, and 5) adjusting, in response to the instruction, the control parameter.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Modular auditory prosthesis systems and methods are described herein. As will be described in detail below, an exemplary auditory prosthesis system includes a sound processor module configured to operate in accordance with a plurality of control parameters and one or more accessory header modules configured to be selectively coupled to the sound processor module and facilitate external adjustment of one or more control parameters included in the plurality of control parameters while coupled to the sound processor module. The one or more accessory header modules may include, but are not limited to, a control header module configured to facilitate manual adjustment of one or more of the control parameters and a programming header module configured to facilitate fitting of the sound processor module to a patient.

As used herein, a "control parameter" may include any parameter governing an operation of a sound processor module. Exemplary control parameters include, but are not limited to, volume control parameters, microphone sensitivity parameters, program selection parameters, noise reduction parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters.

Numerous advantages may be associated with the systems and methods described herein. For example, the modularity of the various components described herein may facilitate enhanced performance of an auditory prosthesis system, simple and convenient expansion and removal of features associated with the auditory prosthesis system, and a more functional and aesthetically pleasing experience for a user of the auditory prosthesis system.

Figure 1:
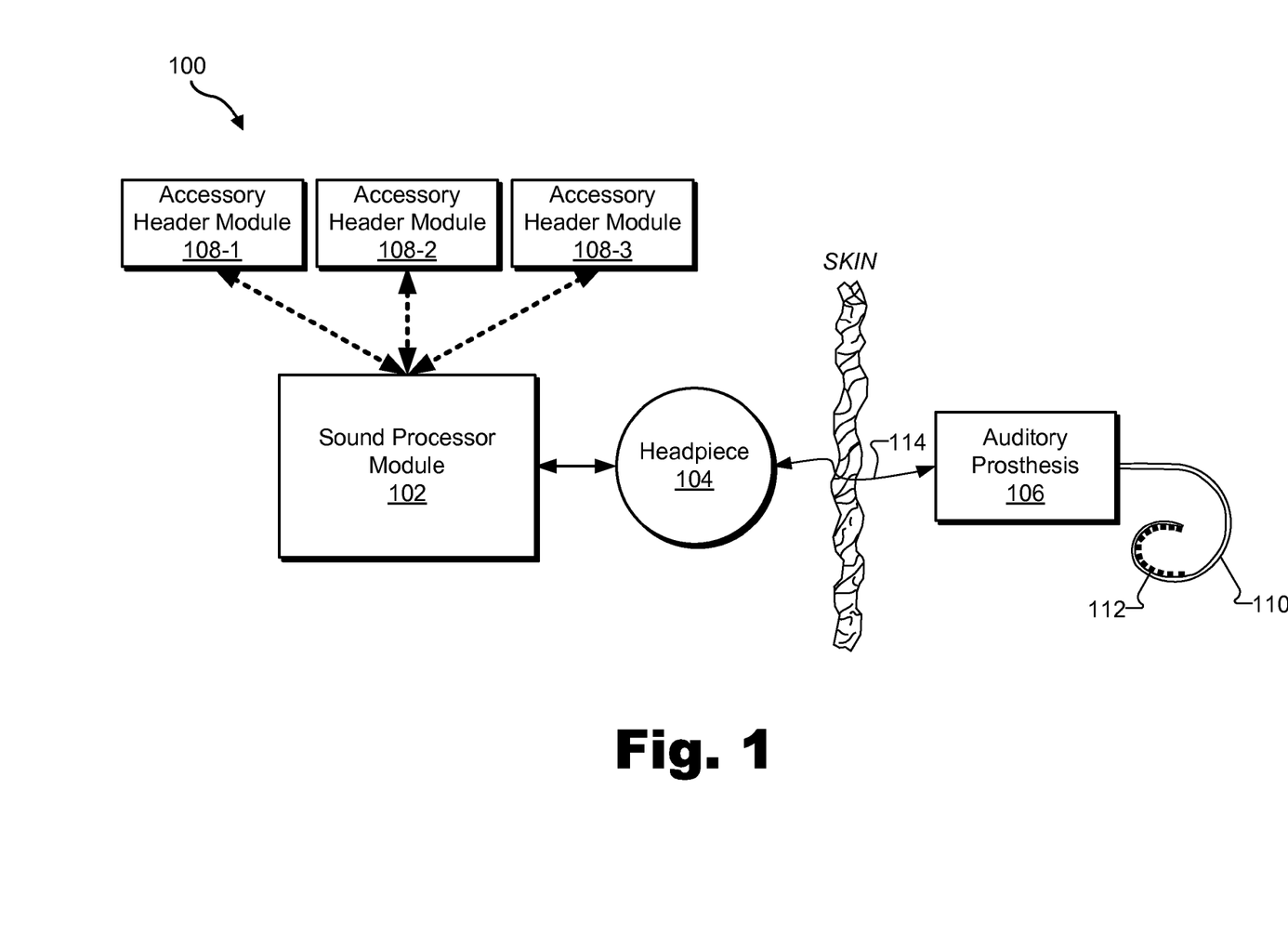
FIG. 1 illustrates an exemplary auditory prosthesis system according to principles described herein.

FIG. 1 illustrates an exemplary auditory prosthesis system 100. Auditory prosthesis system 100 may include a sound processor module 102, a headpiece 104, an auditory prosthesis 106, and one or more accessory header modules 108 (e.g., accessory modules 108-1 through 108-3) configured to be selectively coupled to sound processor module 102. Auditory prosthesis system 100 may further include a lead 110 coupled to auditory prosthesis 106 and having a plurality of electrodes 112 disposed thereon. As shown in FIG. 1, sound processor module 102, headpiece 104, and accessory header modules 108 may be located external to an auditory prosthesis patient. Auditory prosthesis 106, lead 110, and electrodes 112 may be implanted within the patient. As will be described in more detail below, additional or alternative components may be included within auditory prosthesis system 100 as may serve a particular implementation.

In some examples, sound processor module 102 is configured to be worn off the ear of a patient. In other words, sound processor module 102 may be worn or carried by a patient at any location other than behind or on the ear. For example, sound processor module 102 may be secured to a piece of clothing worn by the patient, carried in a pocket or pouch, and/or otherwise carried by the patient. Because sound processor module 102 is not worn behind or on the ear, sound processor module 102 may be relatively larger than typical behind-the-ear sound processors and may therefore include additional or enhanced features compared to such typical behind-the-ear sound processors. In some examples, sound processor module 102 is water proof or at least water resistant.

Sound processor module 102 may be configured to operate in accordance with a plurality of control parameters. For example, sound processor module 102 may operate in accordance with some or all of the control parameters described above. To illustrate, sound processor module 102 may process an audio signal (which may be detected by a microphone, input by way of an auxiliary audio input port, etc.) in accordance with one or more control parameters (e.g., that may be associated with a particular sound processing strategy). Sound processor module 102 may then direct auditory prosthesis 106 to generate and apply electrical stimulation (also referred to herein as "stimulation current") representative of the audio signal to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway.

In some examples, sound processor module 102 may wirelessly transmit stimulation parameters and/or power signals to auditory prosthesis 106 by way of a communication link 114 between headpiece 104 and auditory prosthesis 106. It will be understood that communication link 114 may include a bi-directional communication link and/or one or more dedicated uni-directional communication links. In some alternative embodiments, sound processor module 102 and auditory prosthesis 106 may be directly connected with one or more wires or the like.

Headpiece 104 may be configured to be affixed to a patient's head and positioned such that a coil housed within headpiece is communicatively coupled to a corresponding coil included within auditory prosthesis 106. In this manner, control parameters and power signals may be wirelessly transmitted between sound processor module 102 and auditory prosthesis 106 via communication link 114.

Headpiece 104 may further include a microphone, which may be selectively used to detect one or more audio signals for processing by sound processor module 102. Headpiece 104 may include additional or alternatively components as may serve a particular implementation.

Auditory prosthesis 106 may include any type of implantable stimulator that may be used in association with the systems and methods described herein. For example, auditory prosthesis 106 may include an implantable cochlear stimulator. In some alternative implementations, auditory prosthesis 106 may include a brainstem implant and/or any other type of auditory prosthesis that may be implanted within a patient and configured to apply stimulation to one or more stimulation sites located along an auditory pathway of a patient.

In some examples, auditory prosthesis 106 may be configured to generate electrical stimulation representative of an audio signal detected by microphone 102 in accordance with one or more stimulation parameters transmitted thereto by sound processor module 102. Auditory prosthesis 106 may be further configured to apply the electrical stimulation to one or more stimulation sites within the patient via one or more electrodes 112 disposed along lead 110. In some examples, auditory prosthesis 106 may include a plurality of independent current sources each associated with a channel defined by one or more of electrodes 112. In this manner, different stimulation current levels may be applied to multiple stimulation sites simultaneously by way of multiple electrodes 112. In such examples, auditory prosthesis system 100 may be referred to as a "multi-channel auditory prosthesis system."

Accessory header modules 108 may each include one or more components that facilitate flexible and interchangeable feature expansion of sound processor module 102. Exemplary accessory header modules 108 will be described in more detail below.

In some examples, only one accessory header module 108 may be coupled to sound processor module 102 at a time. For example, sound processor module 102 may include a header interface assembly configured to receive one accessory header module 108 at a time. The header interface assembly may be configured in any suitable manner. For example, the header interface assembly may include a plurality of exposed contacts (i.e., a plurality of contacts disposed on an outer surface of sound processor module 102). Each accessory header module 108 may include a corresponding plurality of connector pins configured to selectively make contact with the exposed contacts when coupled to sound processor module 102. In alternative embodiments, multiple accessory header modules 108 may be coupled to sound processor module 102 at the same time. As will be described in more detail below, sound processor module 102 may be configured to supply power to an accessory header module 108 that is coupled thereto.

In some examples, one or more of accessory header modules 108 may be configured to be selectively coupled to sound processor module 102 by hot plugging into sound processor module 102. In other words, an accessory header module 108 may be plugged into sound processor module 102 while sound processor module 102 is powered on and operating and immediately start functioning. Accordingly, accessory header modules 108 may be hot swappable. In other words, an accessory header module (e.g., accessory header module 108-1) that is coupled to sound processor module 102 may be replaced with another accessory header module (e.g., accessory header module 108-2) without having to power down sound processor module 102.

Exemplary components and implementations of sound processor module 102, auditory prosthesis 106, and accessory header modules 108 will now be described. It will be recognized that the exemplary components and implementations described herein are merely illustrative of the many different components and implementations that may be realized in accordance with the systems and methods described herein.

Figure 2:
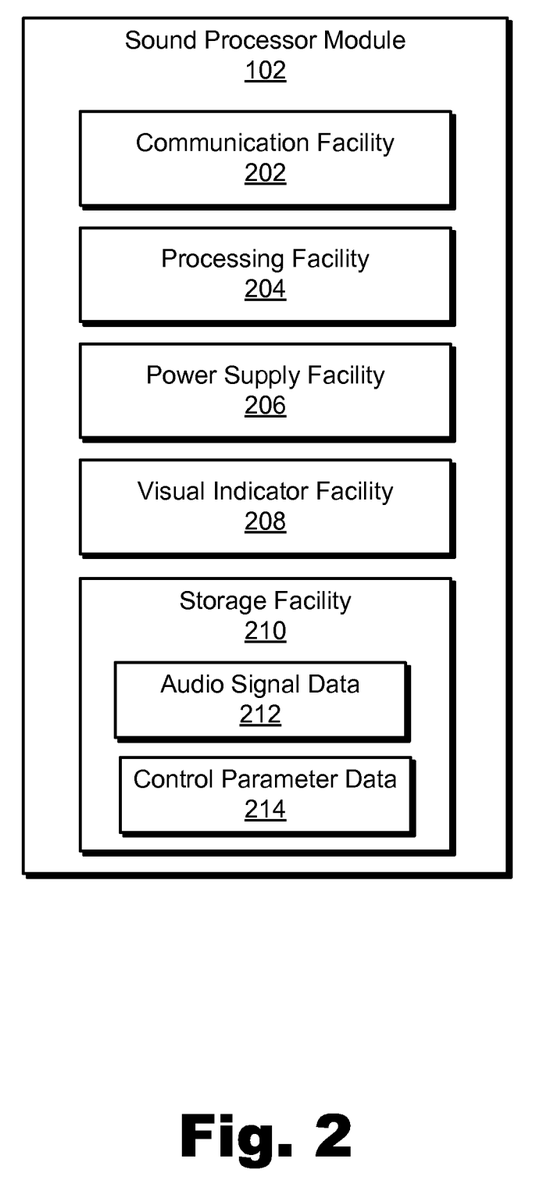
FIG. 2 illustrates exemplary functional components of a sound processor module according to principles described herein.

FIG. 2 illustrates exemplary functional components of sound processor module 102. As shown in FIG. 2, sound processor module 102 may include a communication facility 202, a processing facility 204, a power supply facility 206, a visual indicator facility 208, and a storage facility 210, any or all of which may be in communication with one another using any suitable communication technologies. Each of these facilities will now be described in more detail.

Communication facility 202 may be configured to facilitate communication between sound processor module 102 and accessory header modules 108. For example, communication facility 202 may be implemented by one or more components (e.g., the header interface assembly described above) configured to facilitate electrical coupling of one or more accessory modules 108 to sound processor module 102.

Communication facility 202 may be further configured to facilitate communication between sound processor module 102 and auditory prosthesis 106 by way of headpiece 104. For example, communication facility 202 may be implemented by one or more transceiver components configured to wirelessly transmit data (e.g., control parameters and/or power signals) to auditory prosthesis 106 and/or wirelessly receive data from auditory prosthesis 106.

Processing facility 204 may be configured to operate in accordance with any of the control parameters described herein. For example, processing facility 204 may perform one or more signal processing heuristics on an audio signal presented to a patient. Such signal processing heuristics may include, but are not limited to, one or more pre-processing operations, spectral analysis operations, noise reduction operations, mapping operations, and/or any other types of signal processing operations with respect to a detected audio signal. In some examples, processing facility 204 may generate and/or adjust one or more control parameters governing an operation of auditory prosthesis 106 (e.g., one or more stimulation parameters defining the stimulation pulses to be generated and applied by auditory prosthesis 106).

Power supply facility 206 may be configured to provide operating power to one or more components included within sound processor module 102. Additionally or alternatively, power supply facility 206 may provide operating power to one or more accessory header modules 108 while the one or more accessory header modules 108 are coupled to sound processing module 102.

To illustrate, power supply facility 206 may detect a coupling of an accessory header module 108 to sound processor module 102 and, in response, automatically enable a power supply to accessory header module 108. When accessory header module 108 is decoupled from sound processor module 102, power supply facility 206 may disable the power supply. In this manner, the exposed contacts that are a part of the header interface assembly may be electrically inactive when no accessory header module 108 is coupled to sound processor module 102, thereby minimizing a risk of corrosion of the exposed contacts. An exemplary manner in which power supply facility 206 may detect a coupling of accessory header module 108 to sound processor module 102 will be described below.

Visual indicator facility 208 may be configured to visually indicate an alarm condition of sound processor module 102 and/or an accessory header module 108 coupled to sound processor module 102. Visual indicator facility 208 may be configured to indicate any other status condition of sound processor module 102 and/or an accessory header module 108 coupled to sound processor module 102. In some examples, visual indicator facility 208 may be implemented by one or more light emitting diodes ("LEDs").

Storage facility 210 may be configured to maintain audio signal data 212 representative of an audio signal processed by processing facility 204 and control parameter data 214 representative of one or more control parameters by which sound processing module 102 operates. Storage facility 210 may be configured to maintain additional or alternative data as may serve a particular implementation.

Figure 3:
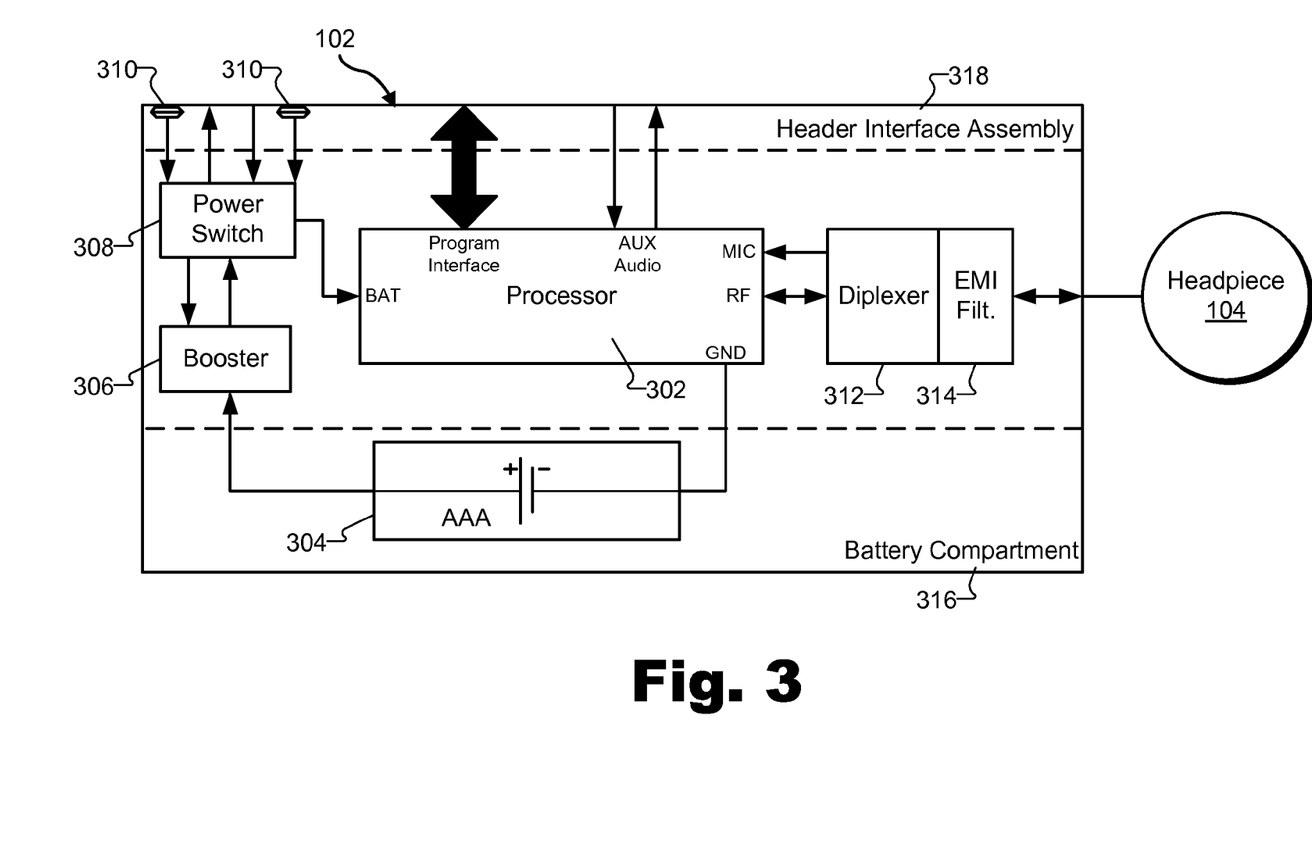
FIG. 3 illustrates an exemplary electrical block diagram of a sound processor module according to principles described herein.

FIG. 3 illustrates an exemplary electrical block diagram of sound processor module 102. Facilities 202-210 may each be implemented by one or more of the electrical components illustrated in FIG. 3. It will be recognized that sound processor module 102 may include additional or alternative electrical components as may serve a particular implementation.

As shown, sound processor module 102 may include a processor 302, a power supply 304, a booster 306, a power switch 308, one or more magnetic sensors 310, a diplexer 312, and an EMI filter 314. Power supply 304 may be housed within a battery compartment 316. Magnetic sensors 310 may be included within a header interface assembly 318 configured to facilitate coupling of an accessory header module 108 to sound processor module 102. Each of these components will now be described.

Processor 302 may be configured to perform any of the signal processing heuristics described herein. To this end, processor 302 may receive various types of input signals such as, but not limited to, a battery input signal, an auxiliary audio input signal, a program interface input signal for communicating with one or more accessory header modules 108, a microphone input signal, an RF input signal, and/or any other type of input signal as may serve a particular implementation. Processor 302 may also provide one or more output signals such as, but not limited to, an audio out signal, one or more RF output signals (e.g., one or more signals to be transmitted to auditory prosthesis 106), one or more program interface signals (e.g., one or more output signals to be transmitted to an accessory header module 108), and/or any other type of output signal as may serve a particular implementation.

Power supply 304 may include any type of power supply as may serve a particular implementation. For example, power supply 304 may include a battery (e.g., a AAA battery), which may be accessible by opening battery compartment 316.

Booster 306 may include any type of boost regulator configured to step a voltage output by power supply 304 to levels required by one or more components within sound processor module 102 and/or an accessory header module 108. For example, power supply 304 may output a voltage substantially equivalent to 0.8-1.5 volts. Booster 306 may step this voltage level up to approximately 3.5 volts or any other voltage level as may serve a particular implementation.

Power switch 308 may be configured to select between power supply 304 and an external power supply (e.g., a power supply provided by way of a clinician's programming interface ("CPI") device). In other words, in some configurations, power switch 308 may cause components within sound processor module 102 to use power provided by power supply 304, while in other configurations, power switch 308 may cause components within sound processor module 102 to use power provided by a power supply 304.

Power switch 308 may be further configured to selectively enable or disable power provided to an accessory header module 108 coupled to sound processor module 102. For example, magnetic sensors 310 may detect a change in an electromagnetic field that occurs as an accessory header module 108 (e.g., one that includes at least one magnet disposed thereon) approaches sound processor module 102 to be coupled thereto. In response to the detecting of the change in the electromagnetic field, magnetic sensors 310 may direct power switch 308 to enable a power supply to the accessory header module 108. Magnetic sensors 310 may be further configured to sense another change in the electromagnetic field that occurs as the accessory header module 108 is decoupled from sound processor module 102 and direct power switch 308 to disable the power supply to the accessory header module 108.

Diplexer 312 and EMI filter 314 may be configured to facilitate communication between sound processor module 102 and auditory prosthesis 106 by way of headpiece 104. For example, diplexer 304 and EMI filter 314 may include one or more transceiver components configured to facilitate wireless communication.

Figure 4:
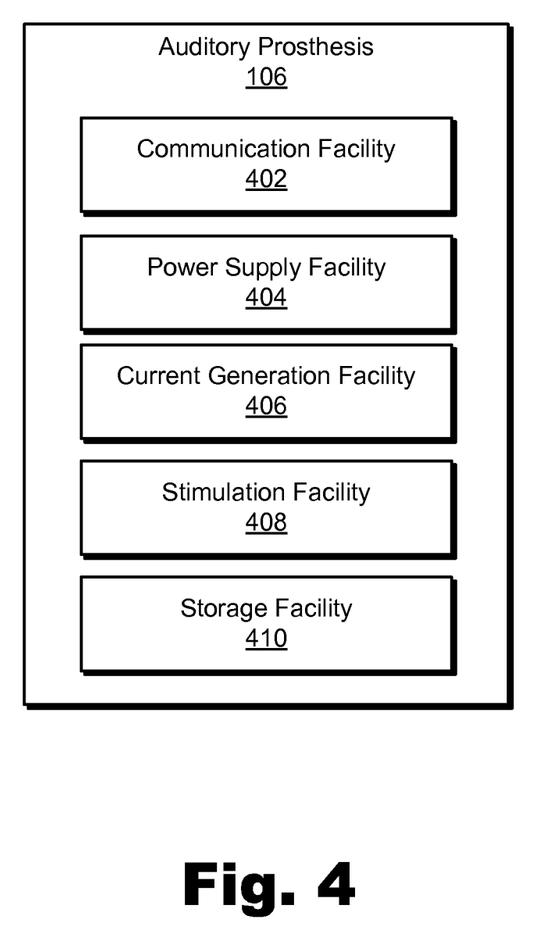
FIG. 4 illustrates exemplary functional components of an auditory prosthesis according to principles described herein.

FIG. 4 illustrates exemplary functional components of auditory prosthesis 106. As shown in FIG. 4, auditory prosthesis 106 may include a communication facility 402, a power supply facility 404, a current generation facility 406, a stimulation facility 408, and a storage facility 410, any or all of which may be in communication with one another using any suitable communication technologies. Each of these facilities will now be described in more detail.

Communication facility 402 may be configured to facilitate communication between auditory prosthesis 106 and sound processor module 102. For example, communication facility 402 may include one or more coils configured to receive control signals and/or power signals from sound processor module 102. Communication facility 402 may additionally or alternatively be configured to transmit one or more status signals and/or other data to sound processor module 102.

Power supply facility 404 may be configured to provide power to various components included within auditory prosthesis 106. To this end, power supply facility 404 may be configured to derive a compliance voltage from a power signal received from sound processor module 102. The compliance voltage may be used by current generation facility 404 to generate stimulation current and/or by any other component within auditory prosthesis 106.

Current generation facility 406 may be configured to generate stimulation current in accordance with one or more stimulation parameters received from sound processor module 102. To this end, current generation facility 406 may include one or more current generators and/or any other circuitry configured to facilitate generation of stimulation current. For example, current generation facility 406 may include an array of independent current generators each corresponding to a distinct electrode or channel.

Stimulation facility 408 may be configured to facilitate application of the stimulation current generated by current generation facility 406 to one or more stimulation sites within the patient in accordance with one or more stimulation parameters received from sound processor module 102. To this end, stimulation facility 408 may be configured to interface with one or more electrodes disposed on a lead that may be inserted within the patient (e.g., within the cochlea).

Storage facility 410 may be configured to maintain data generated and/or utilized by auditory prosthesis 106. For example, storage facility 410 may maintain data representative of one or more stimulation parameters configured to define the stimulation current generated and applied by auditory prosthesis 106.

Exemplary accessory header modules 108 will now be described. It will be recognized that additional or alternative accessory header modules 108 may be used in accordance with the systems and methods described herein as may serve a particular example.

Figure 5A:
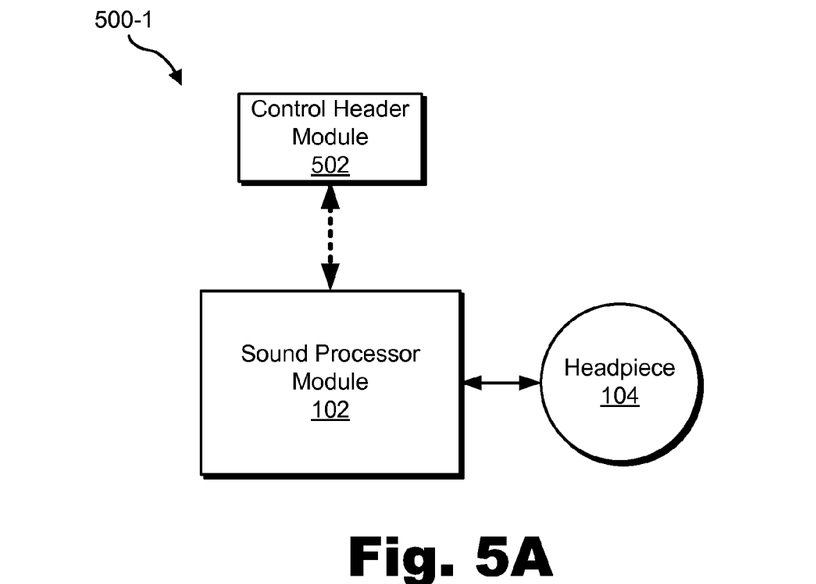
FIGS. 5A-5B illustrate exemplary implementations of the auditory prosthesis system of FIG. 1 according to principles described herein.
Figure 5B:
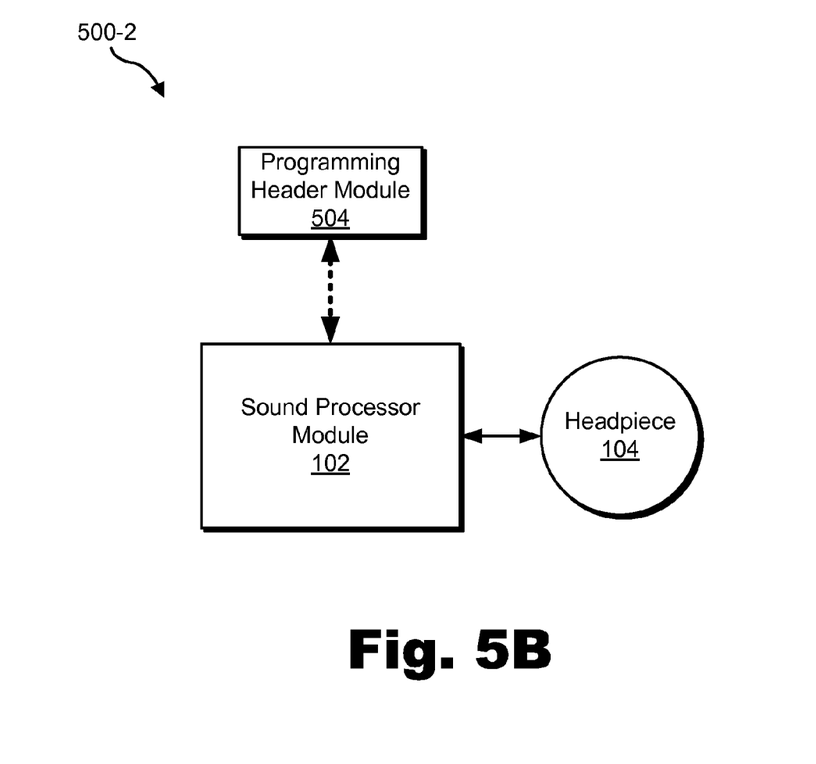

FIG. 5A illustrates an exemplary implementation 500-1 of auditory prosthesis system 100 in which one of accessory header modules 108 includes a control header module 502. FIG. 5B another exemplary implementation 500-2 of auditory prosthesis system 100 in which one of accessory header modules 108 includes a programming header module 504. As illustrated by the dashed lines in FIGS. 5A and 5B, control header module 502 and programming header module 504 may each be configured to selectively couple to sound processor module 1 02 as described above. FIGS. 5A and 5B also show that sound processor module 102 may be communicatively coupled to headpiece 108, which may be communicatively coupled to auditory prosthesis 106 as described above in connection with FIG. 1. Control header module 502 and programming header module 504 will now be described in more detail.

Figure 6:
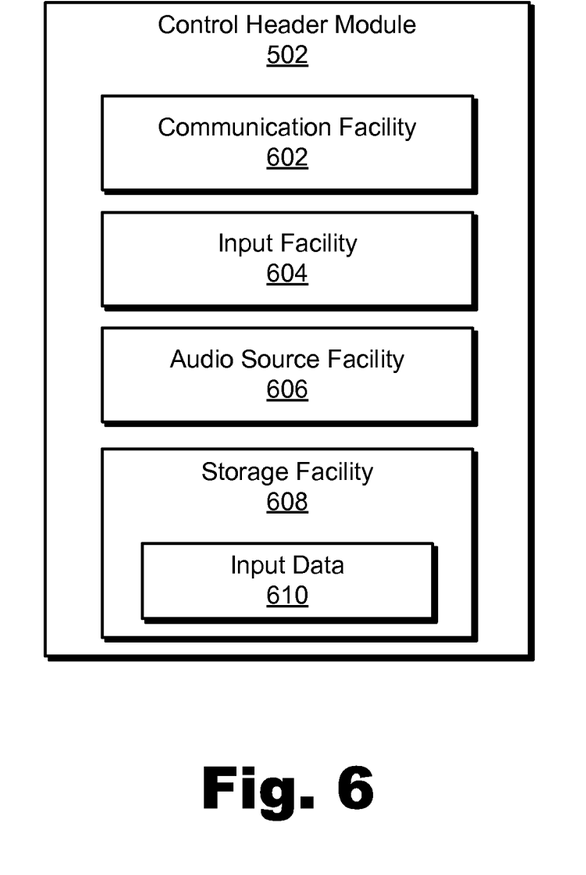
FIG. 6 illustrates exemplary functional components of a control header module according to principles described herein.

Control header module 502 may be configured to facilitate manual adjustment of one or more control parameters governing an operation of sound processor module 102. FIG. 6 illustrates exemplary functional components of control header module 502. As shown in FIG. 6, control header module 502 may include a communication facility 602, an input facility 604, audio source facility 606, and a storage facility 608, any or all of which may be in communication with one another using any suitable communication technologies. Each of these facilities will now be described in more detail.

Communication facility 602 may be configured to facilitate communication between control header module 502 and sound processor module 102. For example, communication facility 602 may be implemented by one or more components configured to facilitate electrical coupling (e.g., hot plugging) of control header module 502 to sound processor module 102.

Input facility 604 may be configured to adjust one or more control parameters governing an operation of sound processor module 102 in response to manual input while control header module 502 is coupled to sound processor module 102. For example, input facility 604 may be configured to adjust a volume parameter, a sensitivity parameter (e.g., a microphone sensitivity parameter), and a program selection parameter, and/or any other control parameter associated with sound processor module 102 while control header module 502 is coupled to sound processor module 102. To this end, input facility 604 may be implemented by at least one control knob, a program selection switch, and/or any other suitable input means. In some examples, control header module 502 may include multiple input facilities 604.

In some examples, the one or more control parameters adjustable by input facility 604 may only be adjusted while control header module 502 is coupled to sound processor module 102. In other words, a user may not adjust the one or more control parameters unless control header module 502 is coupled to sound processor module 102. Such a configuration may be advantageous when auditory prosthesis system 100 is used by a child. The one or more control parameters may be adjusted in a controlled setting (e.g., by a parent or clinician) while control header module 502 is coupled to sound processor module 102. Control header module 502 may then be decoupled from sound processor module 102, thereby preventing the child from inadvertently adjusting the one or more control parameters during normal use.

Audio source facility 606 may be configured to provide one or more alternative audio sources to sound processor module 102 while control header module 502 is coupled to sound processor module 102. For example, audio source facility 606 may provide an auxiliary audio input and/or an FM audio input into sound processor module 102 while control header module 502 is coupled to sound processor module 102.

Storage facility 608 may be configured to maintain input data 610 utilized by input representative of one or more manual user input commands provided by a user by way of input facility 604. Storage facility 608 may be configured to maintain additional or alternative data as may serve a particular implementation.

Figure 7:
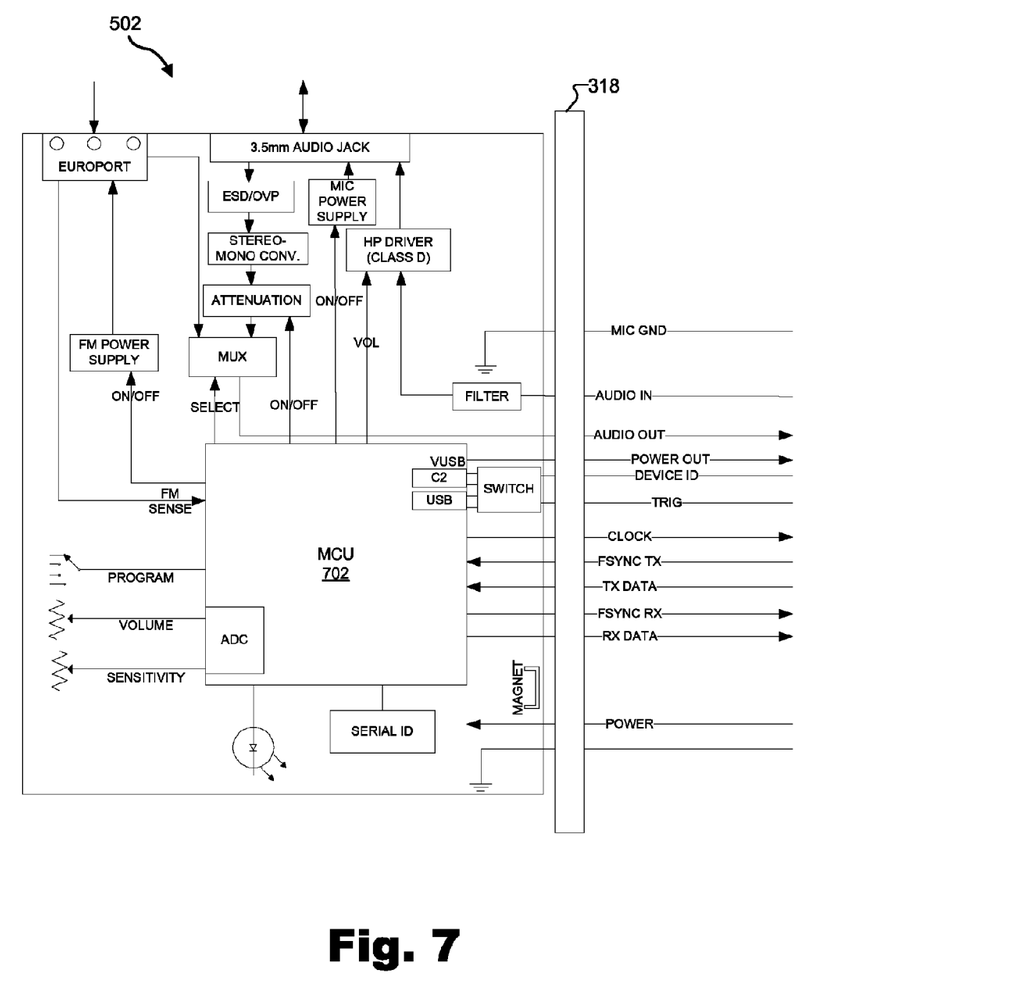
FIG. 7 illustrates an exemplary electrical block diagram of a control header module according to principles described herein.

FIG. 7 illustrates an exemplary electrical block diagram of control header module 502. Facilities 602-608 may each be implemented by one or more of the electrical components illustrated in FIG. 7. It will be recognized that control header module 102 may include additional or alternative electrical components as may serve a particular implementation.

As shown, the electrical components included within control header module 502 may include a microcontroller ("MCU") 702 and various other electrical components configured to perform one or more of the functions associated with control header module 502. For example, MCU 702 and one or more other components shown in FIG. 7 may facilitate manual adjustment of a volume parameter, a sensitivity parameter, and a program selection parameter, selectively provide an FM audio input for use by sound processor module 102, and selectively provide an auxiliary audio input for use by sound processor module 102. To this end, various input and output signal that may be communicated between control header module 502 and sound processor module 102 by way of header interface assembly 318 are also shown in FIG. 7.

Figure 8:
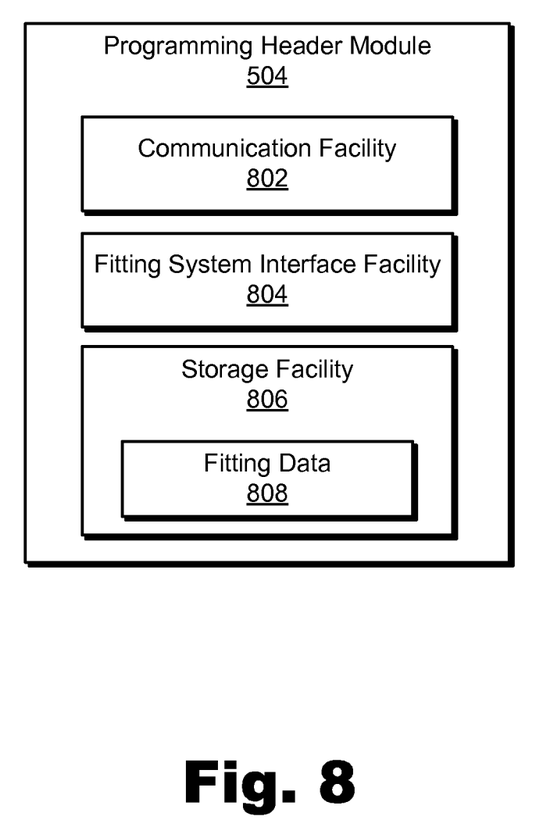
FIG. 8 illustrates exemplary functional components of a programming header module according to principles described herein.

Programming header module 504 may be configured to facilitate a fitting of sound processor module 102 to a patient. To this end, FIG. 8 illustrates exemplary functional components of programming header module 504. As shown in FIG. 8, programming header module 504 may include a communication facility 802, a fitting system interface facility 804, and a storage facility 806, any or all of which may be in communication with one another using any suitable communication technologies. Each of these facilities will now be described in more detail.

Communication facility 802 may be configured to facilitate communication between programming header module 504 and sound processor module 102. For example, communication facility 802 may be implemented by one or more components configured to facilitate electrical coupling (e.g., hot plugging) of programming header module 504 to sound processor module 102.

Fitting system interface facility 804 may be configured to facilitate communication between a fitting system (e.g., a computing device) and sound processor module 102. In this manner, the fitting system may be used to fit sound processor module 102 to a patient. In other words, the fitting system may be used to adjust one or more control parameters governing an operation of sound processor module 102 to optimum values for the patient.

Storage facility 806 may be configured to maintain fitting data 808 utilized during a fitting of sound processor module 102 to a patient. Storage facility 806 may be configured to maintain additional or alternative data as may serve a particular implementation.

Figure 9:
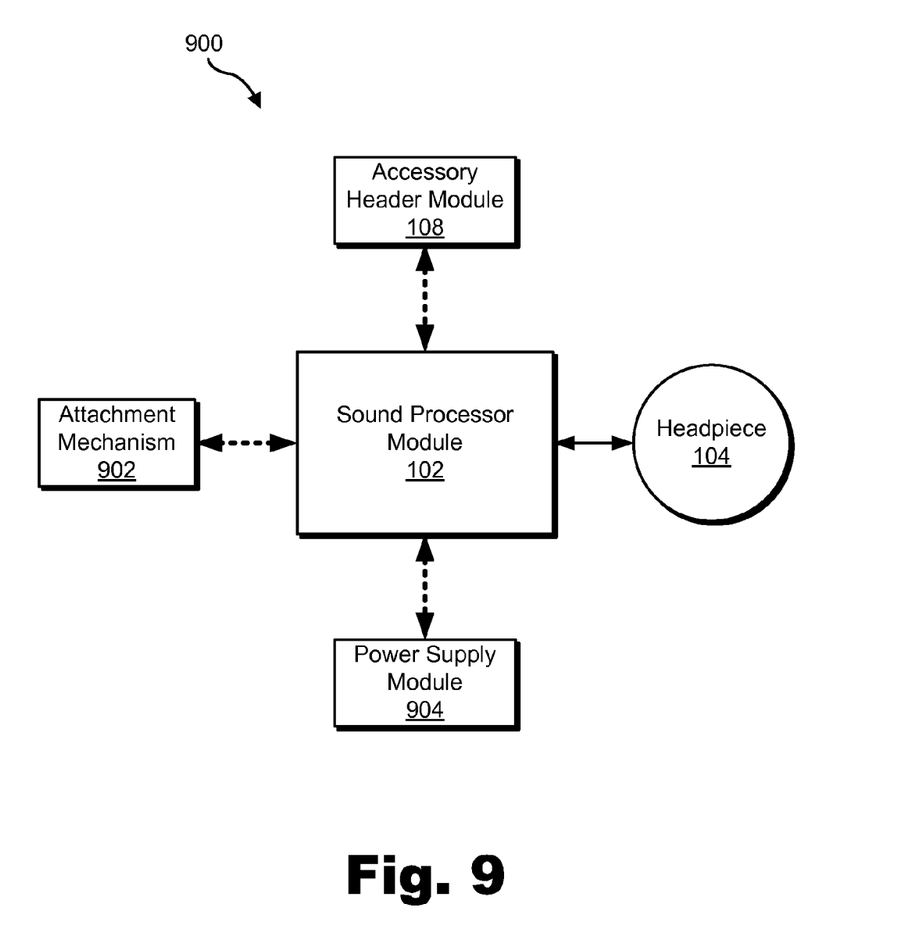
FIG. 9-10 illustrate exemplary implementations of the auditory prosthesis system of FIG. 1 according to principles described herein.

FIG. 9 illustrates an exemplary implementation 900 of auditory prosthesis system 100 in which an attachment mechanism 902 and a power supply module 904 are selectively coupled to sound processor module 102.

Attachment mechanism 902 may be configured to facilitate attachment of sound processor module 102 to a patient or an accessory associated with the patient. For example, attachment mechanism 902 may include, but is not limited to, one or more clips (e.g., collar clips, hair clips, etc.), a pouch, and/or any other means for allowing a patient to wear or carry sound processor module 102. In some examples, attachment mechanism 902 is configured to secure sound processor module 102 with or without an accessory header module 108 coupled to sound processor module 102. Attachment mechanism 902 may additionally be configured to secure sound processor module 102 to the patient while the patient is in water (e.g., swimming or bathing).

Power supply module 904 may include any modular unit configured to be selectively coupled to sound processor module 102. In some examples, power supply module 904 may take the place of batter compartment 316. A modular power supply module may be desirable in some situations where different types and/or sizes of batteries are to be used to provide power to sound processor module 102.

Figure 10:
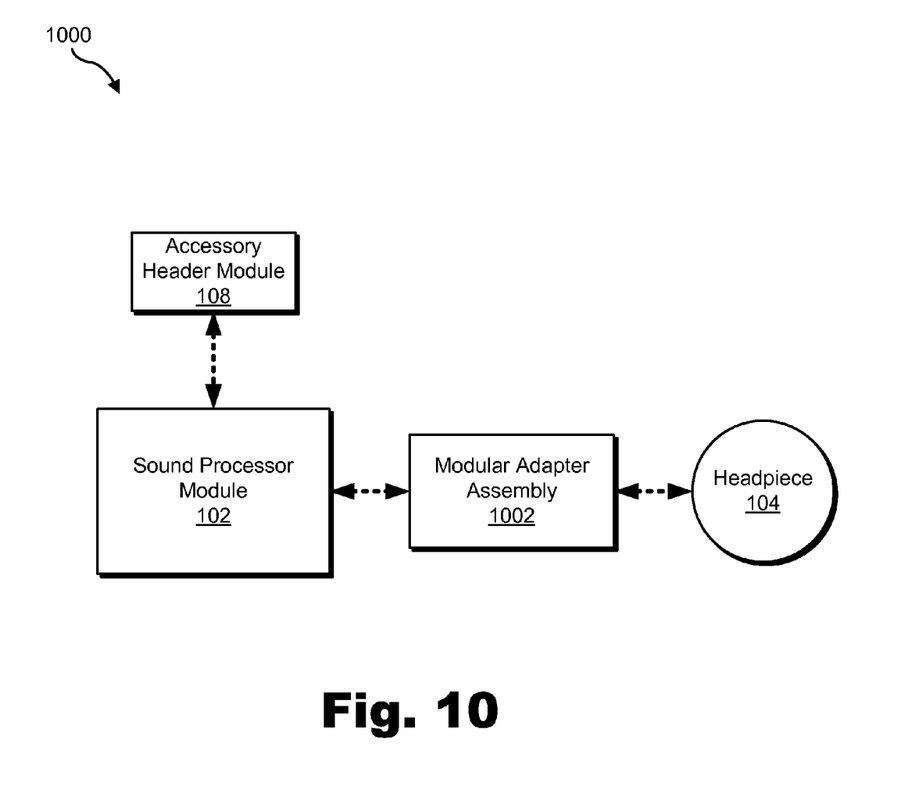

FIG. 10 illustrates another exemplary implementation 1000 of auditory prosthesis system 100 in which a modular adapter assembly 1002 is configured to be selectively coupled in series between sound processor module 102 and headpiece 104. Modular adapter assembly 1002 is configured to facilitate selective use by a patient of at least one of an auxiliary microphone (e.g., a T-MIC by Advanced Bionics, LLC) positioned proximal to an ear canal of the patient and a telecoil. Modular adapter assembly 1002 is described more fully in a related application 61/439,669 entitled "Modular Adapter Assembly for Telecoil and Auxiliary Audio Input Device Mixing" to Lee F. Hartley et al., is to be filed on the same day as the present application. The application 61/439,669 is incorporated herein by reference in its entirety.

Figure 11:
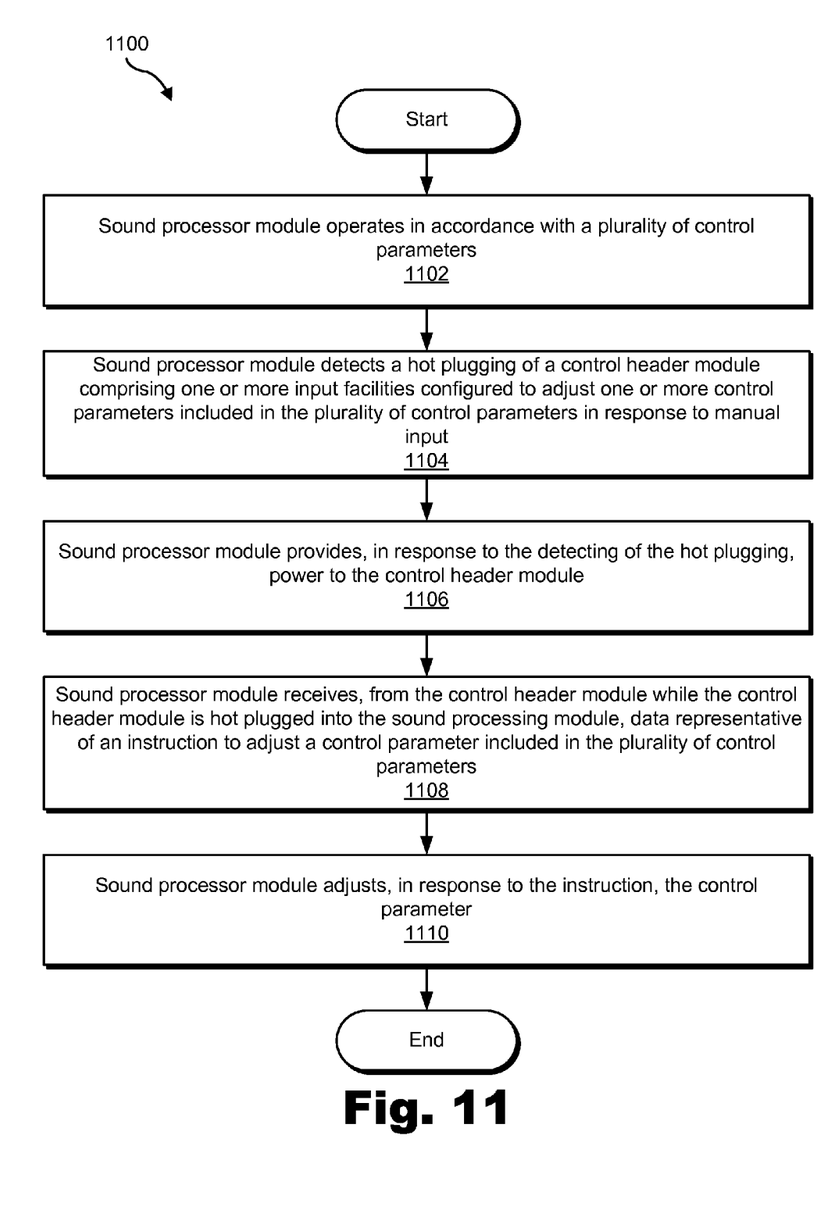
FIG. 11 illustrates an exemplary method of adjusting a control parameter governing an operation of a sound processor module according to principles described herein.

FIG. 11 illustrates an exemplary method 1100 of adjusting a control parameter governing an operation of a sound processor module. While FIG. 11 illustrates exemplary steps according to one embodiment, other embodiments may omit, add to, reorder, and/or modify any of the steps shown in FIG. 11. One or more of the steps shown in FIG. 11 may be performed by any component or combination of components of sound processor module 102.

In step 1102, a sound processor module operates in accordance with a plurality of control parameters. Step 1102 may be performed in any of the ways described herein.

In step 1104, the sound processor module detects a hot plugging of a control header module comprising one or more input facilities configured to adjust one or more control parameters included in the plurality of control parameters in response to manual input. Step 1104 may be performed in any of the ways described herein.

In step 1106, the sound processor module provides, in response to the detecting of the hot plugging, power to the control header module. Step 1106 may be performed in any of the ways described herein.

In step 1108, the sound processor module receives, from the control header module while the control header module is hot plugged into the sound processing module, data representative of an instruction to adjust a control parameter included in the plurality of control parameters. Step 1108 may be performed in any of the ways described herein.

In step 1110, the sound processor module adjusts, in response to the instruction, the control parameter. Step 1110 may be performed in any of the ways described herein.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An auditory prosthesis system comprising:
    a sound processor module configured operate in accordance with a plurality of control parameters and comprising a plurality of contacts disposed on an outer surface of the sound processor module; and
    a control header module configured to be selectively coupled to the sound processor module and comprising
        a plurality of pins configured to make contact with the contacts when the control header module is selectively coupled to the sound processor module, and
        one or more input facilities configured to adjust one or more control parameters included in the plurality of control parameters in response to manual input while the control header module is coupled to the sound processor module;
    a programming header module configured to be selectively coupled to the sound processor module in place of the control header module and comprising
        a plurality of pins configured to make contact with the contacts when the programming header module is selectively coupled to the sound processor module in place of the control header module, and
        a fitting system interface facility configured to facilitate a fitting of the sound processor module to a patient while the programming header module is selectively coupled to the sound processor module in place of the control header module;
    wherein the control header module and the programming header module are hot swappable.

2. The auditory prosthesis system of claim 1, wherein the one or more control parameters are not adjustable while the control header module is not coupled to the sound processor module.

3. The auditory prosthesis system of claim 1, wherein the one or more control parameters comprise at least one of a volume parameter, a sensitivity parameter, and a program selection parameter.

4. The auditory prosthesis system of claim 1, wherein the one or more input facilities comprise at least one of a control knob and a program selection switch.

5. The auditory prosthesis system of claim 1, wherein the control header module is configured to be selectively coupled to the sound processor module by hot plugging into the sound processor module, and wherein the sound processor module is configured to communicate with the control header module in response to the hot plugging without having to power down.

6. The auditory prosthesis system of claim 1, wherein the control header module is further configured to provide at least one of an auxiliary audio input and an FM audio input into the sound processor module while the control header module is coupled to the sound processor module.

7. The auditory prosthesis system of claim 1, wherein the sound processor module is configured to be worn by a patient off the ear of the patient.

8. The auditory prosthesis system of claim 1, wherein the sound processor module comprises circuitry that:
    detects a coupling of the control header module to the sound processor module; and
    enables a power supply to the control header module in response to the detection of the coupling of the control header module to the sound processor module.

9. The auditory prosthesis system of claim 8, wherein the circuitry further:
   detects a decoupling of the control header module from the sound processor module; and
   disables the power supply to the control header module in response to the detection of the decoupling of the control header module from the sound processor module.

10. The auditory prosthesis system of claim 1, further comprising an additional accessory header module configured to be selectively coupled to the sound processor module in place of the control header module and the programming header module.

11. The auditory prosthesis system of claim 1, further comprising an auditory prosthesis configured to be implanted in a patient and communicatively coupled to the sound processor module, wherein the sound processor module is further configured to:
   process an audio signal; and
   direct the auditory prosthesis to apply stimulation representative of the audio signal to one or more stimulation sites within the patient.

12. The auditory prosthesis system of claim 11, further comprising a headpiece configured to be communicatively coupled to the sound processor module and facilitate communication between the sound processor module and the auditory prosthesis.

13. The auditory prosthesis system of claim 12, wherein the headpiece comprises a microphone configured to detect the audio signal.

14. The auditory prosthesis system of claim 12, further comprising a modular adapter assembly configured to be selectively coupled in series between the sound processor module and the headpiece and to facilitate selective use by the patient of at least one of an auxiliary microphone positioned proximal to an ear canal of the patient and a telecoil.

15. The auditory prosthesis system of claim 1, further comprising an attachment mechanism coupled to the sound processor module and configured to facilitate attachment of the sound processor module to a patient or an accessory associated with the patient.

16. The auditory prosthesis system of claim 1, further comprising a power supply module configured to be selectively coupled to the sound processor module and provide power to the sound processor module while the power supply module is coupled to the sound processor module.

17. The auditory prosthesis system of claim 1, wherein the sound processor module comprises a visual indicator facility configured to indicate at least one of an alarm condition and a status condition.

18. A method comprising:
   operating, by a sound processing module, in accordance with a plurality of control parameters;
   detecting, by the sound processing module, a hot plugging of a control header module into the sound processing module, the control header module comprising one or more input facilities configured to adjust one or more control parameters included in the plurality of control parameters in response to manual input;
   communicating, by the sound processing module in response to the detecting of the hot plugging, with the control header module;
   detecting, by the sound processing module, a hot swapping of the control header module with a programming header module that includes a fitting system interface facility configured to facilitate a fitting of the sound processor module to a patient while the programming header module is selectively coupled to the sound processor module in place of the control header module; and
   communicating, by the sound processing module in response to the hot swapping and without first powering down, with the programming header module.

19. The method of claim 18, further comprising:
   preventing, in response the hot swapping, the one or more control parameters from being adjusted.

20. The method of claim 18, embodied as computer-executable instructions on at least one non-transitory computer-readable medium.

21. The auditory prosthesis system of claim 1, wherein the sound processor module:
   detects a hot plugging of the control header module to the sound processor module;
   communicates with the control header module while the control header module is hot plugged to the sound processor module;
   detects, without having to power down, a disconnecting of the control header module to the sound processor module and a hot plugging of the programming header module to the sound processor module in place of the control header module; and
   communicates with the programming header module while the control header module is hot plugged to the sound processor module.

22. The method of claim 18, wherein the communicating with the control header module comprises:
   receiving, from the control header module while the control header module is hot plugged into the sound processing module, data representative of an instruction to adjust a control parameter included in the plurality of control parameters; and
   adjusting, in response to the instruction, the control parameter.

23. A sound processor module comprising:
   at least one processor that
      operates in accordance with a plurality of control parameters,
      detects a hot plugging of a control header module into the sound processing module, the control header module comprising one or more input facilities configured to adjust one or more control parameters included in the plurality of control parameters in response to manual input,
      communicates, in response to the detection of the hot plugging, with the control header module,
      detects a hot swapping of the control header module with a programming header module that includes a fitting system interface facility configured to facilitate a fitting of the sound processor module to a patient while the programming header module is selectively coupled to the sound processor module in place of the control header module, and
      communicates, in response to the hot swapping and without first powering down, with the programming header module.

* * * * *